US012661130B2

(12) United States Patent
Hyttinen

(10) Patent No.: US 12,661,130 B2
(45) Date of Patent: Jun. 23, 2026

(54) DEVICE FOR INTRAMEDULLARY NAILING OF THE TIBIA

(71) Applicant: HEMITEC FINLAND OY, Rusko (FI)

(72) Inventor: Mika Hyttinen, Rusko (FI)

(73) Assignee: HEMITEC FINLAND OY, Rusko (FI)

( * ) Notice: Subject to any disclaimer, the term of this patent is extended or adjusted under 35 U.S.C. 154(b) by 86 days.

(21) Appl. No.: 18/576,691

(22) PCT Filed: May 10, 2022

(86) PCT No.: PCT/IB2022/054316
§ 371 (c)(1),
(2) Date: Jan. 4, 2024

(87) PCT Pub. No.: WO2023/281324
PCT Pub. Date: Jan. 12, 2023

(65) Prior Publication Data
US 2025/0000527 A1 Jan. 2, 2025

(30) Foreign Application Priority Data

Jul. 8, 2021 (FI) ..................................... 20215797

(51) Int. Cl.
A61B 17/72 (2006.01)
A61B 17/17 (2006.01)
A61B 17/64 (2006.01)

(52) U.S. Cl.
CPC ........ A61B 17/1717 (2013.01); A61B 17/645 (2013.01); A61B 17/725 (2013.01)

(58) Field of Classification Search
CPC . A61B 17/64; A61B 17/6408; A61B 17/6425; A61B 17/1717; A61B 17/66;
(Continued)

(56) References Cited

U.S. PATENT DOCUMENTS 2,204,266 A * 6/1940 Wilcox .............. A61B 17/6408
5/624
4,365,624 A * 12/1982 Jaquet ................ A61B 17/6441
606/56
(Continued)

FOREIGN PATENT DOCUMENTS

CA 3014284 C * 1/2021 ......... A61B 17/1642
CN 2880001 Y 3/2007
(Continued)

OTHER PUBLICATIONS

Finnish Patent Office, Search Report for FI 20215797, dated Jan. 24, 2022, 2 pages.

(Continued)

*Primary Examiner* — Jacqueline T Johanas
(74) *Attorney, Agent, or Firm* — Carter, DeLuca & Farrell, LLP

(57) ABSTRACT

The invention relates to a device for intramedullary nailing of the tibia which comprises the frame of a framework which consists of vertical supports (2) and longitudinal (3, 4) and transverse horizontal supports (5, 5', 5'', 6, 6') and a guide (21): which is slidably coupled to the longitudinal horizontal support (4) of the device. The guide (21) comprises a first finder (11) for adjusting the position of the traction needle (20) in the lateral direction, and a second finder (13) for adjusting the position of the traction needle (20) in the vertical direction and for passing the traction needle (20) through the tibia in the transverse direction of the tibia, and attachment arms (22, 24) attached to the frame, to which the ends of the traction needle (20) outside the tibia are attached.

11 Claims, 1 Drawing Sheet

(58) Field of Classification Search
CPC .. A61B 17/645; A61B 17/171; A61B 17/1725
See application file for complete search history.

(56) References Cited

U.S. PATENT DOCUMENTS

| | | | | |
|---|---|---|---|---|
| 4,450,834 | A * | 5/1984 | Fischer | A61B 17/645 |
| | | | | 606/56 |
| 6,328,737 | B1 * | 12/2001 | Moorcroft | A61B 17/66 |
| | | | | 606/57 |
| 6,716,212 | B1 * | 4/2004 | Pickens | A61B 17/864 |
| | | | | 606/54 |
| 11,395,680 | B2 * | 7/2022 | Chen | A61B 17/8866 |
| 11,534,206 | B2 * | 12/2022 | Rodemund | A61B 17/6475 |
| 2001/0051806 | A1 * | 12/2001 | Ballier | A61B 17/8872 |
| | | | | 606/54 |
| 2002/0026190 | A1 * | 2/2002 | Walulik | A61B 17/645 |
| | | | | 606/57 |
| 2009/0014016 | A1 * | 1/2009 | Clifford | A61F 2/08 |
| | | | | 128/898 |
| 2012/0136355 | A1 * | 5/2012 | Wolfson | A61B 17/6408 |
| | | | | 606/54 |
| 2012/0143190 | A1 * | 6/2012 | Wolfson | A61B 17/64 |
| | | | | 606/56 |
| 2013/0066205 | A1 * | 3/2013 | Laster | A61B 17/1725 |
| | | | | 600/439 |
| 2018/0132897 | A1 * | 5/2018 | Shiner | A61B 17/6483 |
| 2019/0000509 | A1 | 1/2019 | Cowens et al. | |
| 2019/0365444 | A1 * | 12/2019 | Federspiel | A61B 17/66 |
| 2021/0059719 | A1 * | 3/2021 | Chen | A61B 17/8872 |
| 2021/0196323 | A1 * | 7/2021 | Chen | A61B 17/6416 |
| 2021/0393294 | A1 * | 12/2021 | Rodemund | A61B 17/6466 |

FOREIGN PATENT DOCUMENTS

| | | | | | |
|---|---|---|---|---|---|
| CN | 106037905 | A | * | 10/2016 | |
| CN | 108272497 | A | * | 7/2018 | A61B 17/60 |
| CN | 208339586 | U | | 1/2019 | |
| CN | 111067603 | A | | 4/2020 | |
| CN | 111956315 | A | | 11/2020 | |
| CN | 112244971 | A | * | 1/2021 | A61B 17/6425 |
| CN | 112890935 | A | | 6/2021 | |
| CN | 113440232 | A | * | 9/2021 | A61B 17/62 |
| CN | 112890935 | B | * | 12/2024 | A61B 17/645 |
| CN | 111067603 | B | * | 4/2025 | A61B 17/6408 |
| GB | 2114891 | A | * | 9/1983 | A61B 17/62 |
| JP | 2002515782 | A | | 5/2002 | |
| JP | 2013521883 | A | | 6/2013 | |
| WO | 9741790 | A2 | | 11/1997 | |
| WO | 2006105673 | A1 | | 10/2006 | |
| WO | WO-2020064814 | A1 | * | 4/2020 | A61B 17/6425 |

OTHER PUBLICATIONS

European Patent Office, International Search Report for PCT/IB2022/054316, dated Sep. 16, 2022, 3 pages.
European Patent Office, Written Opinion of the International Searching Authority, dated Sep. 16, 2022, 6 pages.
Japanese Office Action for application No. 2023-580965 dated Sep. 4, 2025 with English translation, 6 pages.

* cited by examiner

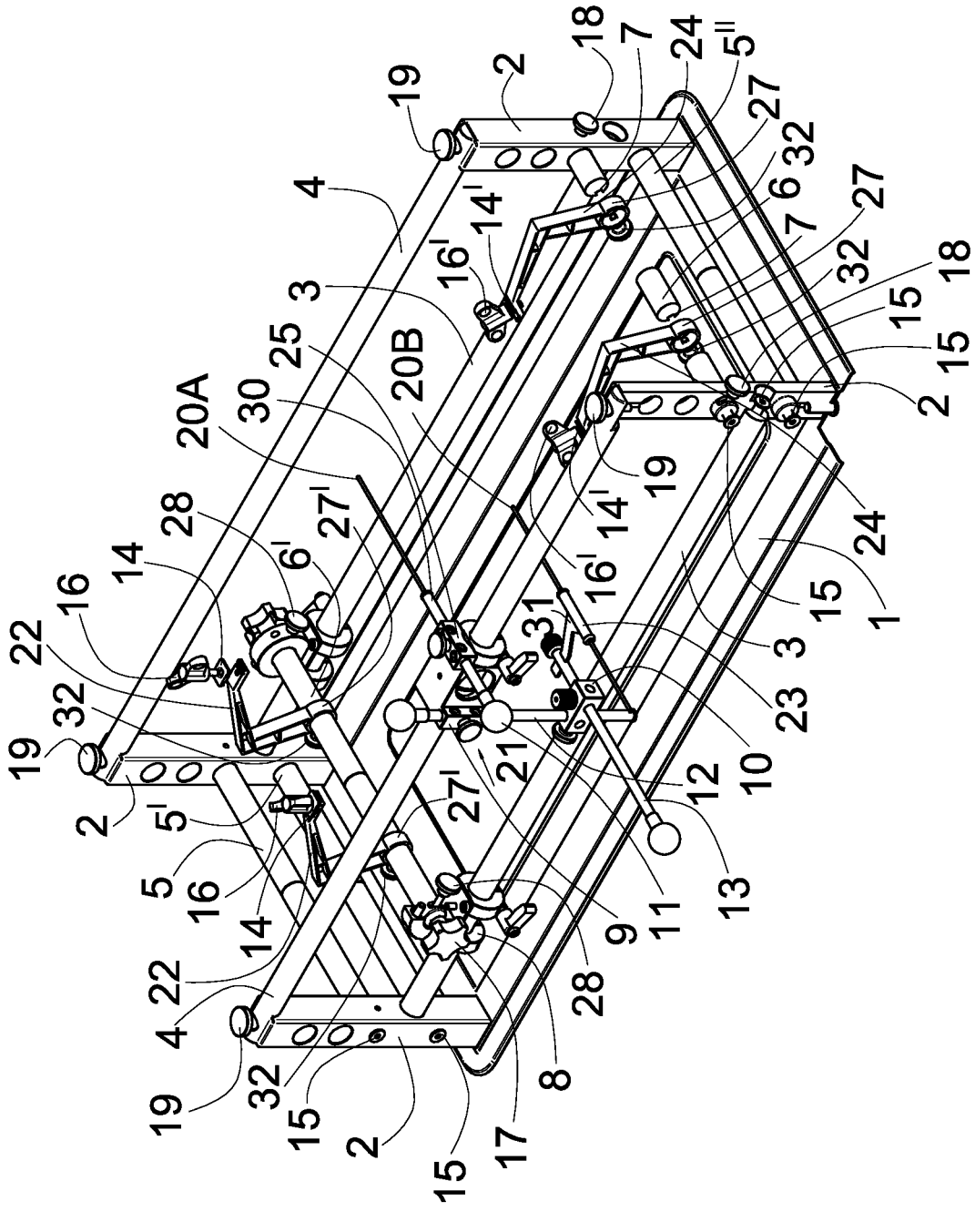

DEVICE FOR INTRAMEDULLARY NAILING OF THE TIBIA

CROSS-REFERENCE TO RELATED APPLICATIONS

The present application is a U.S. national stage application of International Application No. PCT/IB2022/054316, filed May 10, 2022, which claims priority to and the benefit of Finnish Application No. 20215797, filed Jul. 8, 2021, the contents of which are incorporated herein by reference and made a part hereof.

TECHNICAL FIELD

The invention relates to a device for intramedullary nailing of the tibia.

BACKGROUND

A tibial fracture is a common injury especially among young and middle-aged adults. A fracture may be caused by a fall, an accident or a strong blow to the leg. The treatment of a tibial fracture generally involves repositioning, that is, positioning the ends of the bone at the fracture site in place.

Intramedullary nailing is the most commonly used method for treating tibial fractures, which means inserting a metal nail in the medullary cavity of the tibia. The nail is placed in the medullary cavity through a tendon below the patella. Once the nail is in place, screws are inserted through both of its ends to keep the bones in the desired position.

The function of intramedullary nailing of the tibia is to keep the parts of the bone separated by the fracture aligned so that the ends of the bone at the fracture site of the tibia are in line and the tibia will thus ossify into the correct position.

Traditionally, the intramedullary nail is thus inserted inside the bone from the top part of the tibia, which according to studies causes post-procedural pain in the front part of the knee, that is, so-called Anterior Knee Pain symptoms, to a significant number of patients.

Furthermore, in a still commonly used surgical method, the patient's leg to be operated is placed at a more than 90-degree angle against a round support. In addition. Forward and downward traction is applied diagonally to the leg in order to align the ends of the damaged tibia. This procedure may cause the nerves at the back of the knee to become pinched and the risk of nerve damage increases. When using a wedge pillow, an assistant, that is another surgeon, is needed to keep the leg in place. The assistant's task in the procedure is to maintain the required traction in the leg so that the ends of the bone are aligned and the leg is not able to move when space for the intramedullary nail is drilled in the bone.

There are two known versions of intramedullary nailing of the tibia. In the first method, there is used a traction table which is designed for said procedure, but which involves many problems. For example, preparing for surgery is time-consuming and imaging is challenging. The patient may suffer nerve damage if the patient is not positioned correctly, and in this method, the surgeon has to work in an ergonomically demanding working position. In the second method, the intramedullary nailing is performed on a standard operating table using a wedge pillow designed for intramedullary nailing of the tibia. The problem with this procedure is that the leg moves continuously and thus another orthopedist or traumatologist is needed to support the leg during the procedure. In addition, this wedge pillow procedure, in which the leg can move a lot, easily causes tissue damage and vascular damage to the calf muscles.

In a commonly used surgical method, a needle is also drilled through the heel bone and attached to the traction device. There are important nerve structures and soft tissues in the heel bone area, which are more susceptible to damage.

Patent publication CN110537964A is cited as prior art, which discloses a device for intramedullary nailing of the tibia, wherein the length of the bone can be adjusted by means of needles passed through the bone.

The object of the present invention is to provide a device which allows for safer and more patient-friendly tibial intramedullary nailing surgery.

BRIEF DESCRIPTION OF THE INVENTION

The device for intramedullary nailing of the tibia according to the invention comprises the frame of a framework, which consists of vertical supports and longitudinal and transverse horizontal supports. The device also comprises a guide which is slidably coupled to the longitudinal horizontal support of the device. The guide comprises a first finder for adjusting the position of the traction needle (20) in the lateral direction and a second finder for adjusting the position of the traction needle in the vertical direction and for passing the traction needle through the tibia in the transverse direction of the tibia. The device also comprises attachment arms attached to the frame, to which the ends of the traction needle outside the tibia are attached.

The preferred embodiments of the invention have the characteristics described below which are disclosed in the dependent claims.

The device comprises first attachment arms for the traction needle of the lower part of the tibia. The first attachment arms are attached to a transverse support slidably attached between some of the longitudinal supports in the frame. The transverse support slidably attached between the longitudinal supports slides along the longitudinal supports by means of a guide carriage, such as a traction carriage.

The longitudinal horizontal supports usually consist of upper supports and lower supports, in which case the lower supports preferably act as the slide rails for the guide carriage.

The device also comprises second attachment arms for the traction needle of the upper part of the tibia. The second attachment arms are attached in the frame to a transverse support attached between two vertical supports in a fixed manner, that is, non-movably.

The transverse supports can be turned forwards and backwards, which means that the attachment arms attached to them can be turned to forward and rearward positions.

The guide comprises a first finder attached with attachment means and a second finder attached with attachment means for passing the traction needles through the lower part and upper part of the tibia, respectively.

A vertical height adjustment part is connected to the guide, which vertical height adjustment part is attached at its upper part to the said same attachment means or to a separate attachment element in the guide, and at its lower part to a second attachment means. The first finder and the second finder are in the same guide at different adjustable heights.

The attachment arms are attached to the transverse supports by means of rings which encircle them. The rings comprise a threaded hole through which a screw can be tightened to the bottom of a groove to keep the attachment arms in place.

This device according to the invention, which can be called a tibial traction and repositioning device, has been developed for "suprapatellar" (i.e. performed under the patella) intramedullary nailing of the tibia in adult patients. The biggest difference to the existing operating method is that this procedure is performed by using a standard operating table so that the leg is fixed between a tibial traction and repositioning device from the upper and lower part of the tibia, so that the leg is only slightly flexed, and the device is on the operating table on its own support. The conventional method uses a traction table designed for the purpose, for example, an "Ossano" traction table, or alternatively a wedge pillow used on a standard operating table.

In the tibial traction and repositioning device according to the invention, the knee is placed at an angle of approximately 5-10 degrees, which prevents the operation from causing nerve damage to the patient's nerves at the back of the knee, in the "crook", because no pressure is exerted on the back of the leg. The device comprises needle attachment arms for the needles at the upper and lower parts of the tibia. The attachment arms of the needle at the lower part of the tibia are on slide rails and thus by pulling the attachment mechanism of the lower part, the ends of the tibia can be aligned. The attachment arms of the needle at the upper part of the tibia do not move in the longitudinal direction of the device.

In the invention, the tibia is attached to the tibial traction and repositioning device by means of thin needles. The needles are drilled through the bone from the side of the tibia, from the upper and lower parts of the fractured tibia. The advantage of the novel device is that the needles are drilled into already damaged bone, thus sparing intact bones, nerves and tissues from unnecessary damage.

The medico-technical device according to the invention allows for safer and more cost-efficient intramedullary nailing surgery of the tibia. In conventional methods, the intramedullary nailing of the tibia on a pillow requires an additional surgeon for the procedure in order to provide sufficient traction in the leg and to keep the leg in place during the procedure.

The invention is described in greater detail in the following by means of an embodiment and a related figure as well as the use of the embodiment.

FIGURES

FIG. 1 shows the traction and repositioning device of the invention for intramedullary nailing of the tibia.

DETAILED DESCRIPTION

FIG. 1 shows the device according to the invention for tibial traction and repositioning for intramedullary nailing of the tibia, wherein an intramedullary nail is inserted in the tibia.

A tibial fracture inflicted on a patient due to a trauma is treated by means of an intramedullary nail inserted in the tibia and left there if repairing the tibia so requires. This is the case if the bone is fractured into two or more parts and the fractures do not extend to the joint surface.

The patient (not shown) lies on their back on the operating table (not shown) throughout the operation. The patient is anaesthetised for the procedure. The patient is then covered with sterile covering, leaving the leg to be operated exposed.

The device according to the invention has a rectangular base 1. The base 1 is a bottom plate, which is a rectangular plate open in the centre to allow imaging so that there is no metal in the imaging area when imaging from above with respect to the leg. The purpose of the base 1, that is, the bottom plate, is to stabilise the device and to prevent the device from pressing into the soft mattrasses of the operating table. The vertical supports 2 can be attached to the base 1.

Two upper supports 4 are attached to the totally four vertical supports 2, in each corner of the base 1, by means of knurled-head screws 19, approximately at the height of the tibia when the knee is elevated to an angle of approximately 10 degrees. The two upper supports 4 are attached on both sides of which base 1 by extending over its longitudinal sides. In addition, two lower supports 3 extending over longitudinal sides of the base 1 are coupled approximately to the level of the ankle.

Transverse supports 5, 5', 5" and 6, which are attached to the vertical supports 2, for example, by means of screws 15, approximately to the level of the ankle, are coupled on the other two sides of the base 1, by extending over its short sides. The device further comprises a transverse support 6' between the lower supports 3, which moves on a guide carriage 8, such as a traction carriage, along the lower supports 3. The lower supports 3 have thus been constructed to function as slide rails for the guide carriage 8 and support the device.

The vertical supports 2, the upper supports 4, the lower supports 3 and the transverse supports 5, 5', 5", 6 and 6' may be, for example, guides, pipes or rods or corresponding supports or shafts.

In FIG. 1, the lowest transverse supports 5' and 5" are on a somewhat lower level than the lower supports 3, and transverse support 5 and transverse support 6 are on a somewhat higher level than the lower supports 3. Transverse support 6 is drawn discontinuously in FIG. 1 for illustrative purposes to make it easier to see how the attachment arms 24 are attached to it, which will be explained later in the text. Transverse support 6 is a control shaft, the function of which will be explained below. In FIG. 1, the transverse supports 5, 5', 5" and 6 are attached to the vertical supports 2 by means of fastening screws 15 or by another method of attachment. The purpose of the holes (no reference numeral) in the vertical supports 2 is to lighten because the vertical supports 2 are heavy. The transverse supports 5, 5', 5" and 6 are in their fixed positions and the transverse support 6' moves along the lower supports 3 as mentioned above.

The device according to the invention is placed under the leg to be operated in such a way that the patient lies on his back and the leg to be operated on the device is towards shaft 5.

After this, the leg to be operated must still be placed accurately or more accurately in position on the device to stabilise the bone with the fracture.

For stabilisation, so-called traction needles are drilled through the tibia laterally and both in the upper part of the tibia, in the vicinity of the patella, at a point below it, and in the lower part of the tibia, at the ankle. Drilling the traction needles through the tibia takes place by means of a guide attached to an upper support 4. The guide 21 moves along another upper support 4.

The traction needles will be removed before the surgical wound is closed after the operation. Before drilling the traction needles, it, however, has to be ensured that the guide 21 for drilling a traction needle is in the correct position with respect to the bone in both the vertical and lateral directions. The position of the guide 21 is checked with an X-ray machine and adjusted if necessary.

The guide 21 moves unobstructed in the upper support 4 from the ankle to the knee and comprises separate transverse arms 11, 13 at different heights which function as finders for positioning the traction needles. These transverse arms 11, 13 are directionally controlled and not intended to rotate, and thus their shape is preferably other than round, for example, a square, thus locking them better to the sleeve in the lateral direction to prevent rotation.

Positioning the First Traction Needle

The guide 21 comprises a first sleeve 25, through which a first transverse arm 11 passes, transversely to the upper support 4, at the end of which transverse arm 11, there is shown a traction needle 20 in position A, at which its lateral position is adjusted. The traction needle 20 is marked as 20A when it is in position A in the sleeve 30 at the end of the transverse arm 11. The transverse arm 11 functions as the upper finder for the upcoming mounting of the traction needle 20. The purpose of the transverse arm 11, that is, of the upper finder, is to adjust the lateral position of the guide 21, which is done by X-raying from above. The actual drilling of the traction needle 20 through the tibia does not yet take place in position A.

The guide 21 comprises a second sleeve 9, through which passes a height adjustment part 12, the sleeve 9 being in the upper part of the height adjustment part 12. A bar or the like can be used as a height adjustment part 12. In the lower part of the height adjustment part 12, there is a third sleeve 10 through which the height adjustment part 12 of the guide 21 passes. The height adjustment part 12 thus combines the lower finder with the upper finder (i.e. transverse arms 11 and 13).

A second transverse arm 13 passes through sleeve 10, transversely to the upper support 4, to which second transverse arm 13, the traction needle 20 is now attached by means of a connecting piece 31, which comprises a sleeve 23. In other words, the traction needle is transferred from transverse arm 11 to transverse arm 13. Transverse arm 13 functions as a lower finder for the same traction needle 20 which was previously used to check at which point the traction needle 20 was with respect to the joint surface of the upper part of the tibia, that is, its position in the lateral direction was checked and it was then transferred into the sleeve 23 of transverse arm 13.

Thus, after the adjustment of the lateral direction of the guide 21, this same traction needle 20 is drilled through the sleeve 23 of the lower finder and further through either the upper part or lower part of the tibia once it has first been ensured by an X-ray that the traction needle 20 is at the correct height by X-raying from the lateral direction.

It is further emphasised that this traction needle 20 is transferred from the upper finder to the lower finder once the leg has first been X-rayed from above and it has been ensured that the traction needle 20 will not penetrate the joint and remains below the joint surface. The upper finder and the lower finder are positioned on top of one another when viewed from above, and the said finders are aligned on top of one another when the device is viewed from the lateral direction.

When the position of the guide 21 has been ensured and correctly located, the drilling of the traction needle 20 through the bone takes place. This is usually done so that an equal part of it is exposed on each side of the leg.

For drilling through the bone, the traction needle 20 is attached to a separate hand drill (not shown) before it is drilled through the sleeve 23 into the tibia, that is, once the guide 21 and thereby the sleeve 23 have been set to the correct height with respect to the tibia by using the height adjustment part 12. X-raying from above shows how close the needle is to the joint surface.

The traction needle 20 is marked as 20B when it is in position B drilled into the bone. Position B thus describes traction needle 20B in its position B drilled inside the bone. The order of positioning the needles 20 is not relevant, but it is more common to position the traction needle of the upper part of the tibia first. In this embodiment it was, therefore, assumed that the traction needle 20 is first drilled to the upper part of the tibia.

The traction needle 20 in the upper leg is attached at both of its ends, for example, by means of winged screws 16' and clamps 14' to the first attachment arms 24 intended for them, with the leg at a small, approximately 10-degree angle. The attachment arms 24 are in turn attached by means of rings 27 to a fixed transverse support 6, which thus passes through the ring 27.

The attachment arms 24 are attached to a transverse support 6 by means of rings 27 to enable them to turn forwards and backwards. The attachment arms 24 turn along with the transverse support 6 when the screw 18 is loose. The attachment arms 24 can thus be turned into a rear position out of the way when the patient is fitted with a traction needle.

The attachment arms 24 also move slightly laterally along the transverse support 6 when the knurled-head screws 32 are loose.

On the outer surface of the transverse support 6, at the knee end, that is, at the end of the upper leg, there is a groove 7 which remains inside the device.

The purpose of the groove 7 is to enable locking the attachment arms 24 with a tightening screw, such as a knurled-head screw 32, to a position in which they are sufficiently close to the skin for attaching the traction needle to the attachment arms 24. In other words, the attachment arms 24 are first placed close to the skin and then locked with knurled-head screws 32 in the transverse groove 7 on the outer surface of the transverse support 6. The groove 7 prevents the attachment arms 24 from rotating because a part of the tightening screw is at the bottom of the groove 7. If there was no groove 7, tightening the attachment arms 24 against the rounded surface of the transverse support 6 might lead to the arms 24 being able to rotate.

Positioning the Second Traction Needle

Positioning the second traction needle, in this embodiment to the lower part of the tibia, is carried out with the same guide 21 as the first traction needle 20 was positioned to the upper part of the tibia.

When the position of the second traction needle in the longitudinal direction has been adjusted with the upper finder 11, as was done with the first traction needle, the second traction needle is positioned to the end of the transverse arm 13 functioning as the lower finder by means of a connecting piece 31 and the sleeve 23 therein.

Drilling the second traction needle through the tibia in its bottom part at the ankle takes place in the same way as the drilling of the first traction needle 20 to the upper part of the tibia.

Since it is assumed that the Figure shows the first traction needle 20, which is drilled into the upper part of the tibia, the second traction needle has not been given its own reference numeral, but FIG. 1 is exactly equivalent when the question is of positioning the second traction needle, with the exception that the first traction needle 20 is replaced by the second traction needle.

The traction needle of the lower leg is attached at both its ends, for example, by means of wing screws 16 and clamps 14 to second attachment arms 22 intended for them which are attached to the moving transverse support 6', with the leg at a small angle of approximately 10 degrees.

The attachment arms 22 are attached to transverse support 6' by means of rings 27 to enable them to turn forwards and backwards. The attachment arms 22 turn along with the transverse support 6' when the screw 28 is loose. They 22 can thus be turned into a rear position out of the way when the patient is fitted with a traction needle. The movement of the attachment arms 22 forwards and backwards can thus be adjusted with a screw 17, by means of which the transverse support 6' can be rotated.

The attachment arms 22 also move somewhat sideways along the transverse support 6' when knurled-head screws 32 are loose.

To position the traction needle, that is, the traction needle of the lower leg, the attachment arms 22 are first placed close to the skin and then locked with knurled-head screws 32 to the transverse support 6' moving along the lower support 3, in the groove on the outer surface of the transverse support 6', which is not shown in FIG. 1 but is similar to that shown in the transverse support 6. At the end of the ankle, that is, at the lower leg end, the groove remains outside the device.

Once the traction needle is positioned, the screw 17 is turned to the front position and locked with a knurled-head screw 28.

Some additional points of emphasis are disclosed below.

Generally speaking, if the screw 32 is loose, the attachment arms 22 or 24 can be moved laterally on shaft 6 or 6' at the same time when the traction needle 20 is already attached to the attachment arms 22 or 24. The rods 6, 6' and the attachment arms 22, 24 may not under any circumstances move forwards or backwards after the traction needles 20 have been attached. If the screw 32 was so loose that the screw was no longer in the groove 7, then the attachment arms 22, 24 could rotate freely about the shaft 6, 6' but this must not happen.

The purpose of the topmost long upper supports 4 of the device in the longitudinal direction is to stabilise the device. They can also be used to support the leg, for example, by using an X-ray drape during the actual intramedullary nailing procedure or in positioning the traction needles at the very beginning of the procedure. Supporting with an X-ray drape means, for example, that the drape can be placed so that it is attached at both ends of the drape to the upper supports 4 with drape forceps. One end of the drape in one upper support 4 and the other end in the other. In this way, the leg can be placed on the drape/drapes when, for example, placing the traction needles in position, and thus the leg does not need to be supported.

The upper supports 4 are usually on purpose slightly higher than the attachment arms of the traction needles when they are in the front position. This is to keep the upper supports 4 out of the way of the X-raying when imaging from the lateral direction with respect to the leg.

The guide 21 used at the beginning of the procedure is also attached to the upper supports 4. The guide 21 slides on the upper support 4 unobstructed from the knee to the ankle. The guide 21 is always attached to the outermost long upper support 4 with respect to the leg to be operated. A traction needle is drilled through the tibia through the sleeve of the guide 21 which is why it is always positioned in the outermost upper support 4. The guide 21 has two functions: the upper finder 11 and the lower finder 13. The upper finder 11 comprises a transverse rod 30, which is hollow at the end of the rod to allow a traction needle to be placed at the end of the rod. The upper finder 11 shows with an X-ray device, with the help of a traction needle, how far the traction needle is from the joint surface, that is, the X-ray is taken from above with respect to the leg. The lower finder 13 is used to view the correct height for the traction needle with the X-ray device from the lateral direction with respect to the leg. The lower finder 13 also comprises a guide sleeve 23, through which the same traction needle which was first used in the upper finder is drilled through the bone. The lower finder also comprises a height adjustment part 12, for example a vertical rod, by means of which the height of the sleeve with respect to the bone can be adjusted. These two functions, the upper and lower finder, are obviously aligned with respect to each other when the entity is viewed from above.

The upper supports 4 can be detached from the device when the intramedullary nail has been positioned in the tibia, but this is not necessary. The device can be constructed so that the upper supports 4 are not in the way when fastening screws are placed on the nail.

In addition to stabilising the device, the long lower supports 3 also act as slide rails for the guide carriage 8, or traction carriage, at the ankle end. The carriage allows the right amount of traction to be exerted on the leg for aligning the ends of the bone and to lock the guide carriage 8 to the lower support 3 so that it cannot move by itself.

The lower transverse supports 5' and 5" are so-called fixed transverse supports and they can be removed, if necessary, but their purpose is to stabilise the device. The total of two attachment arms 24 of the traction needles are attached to the upper transverse support 6. There is also a milled grooving at both ends of the transverse support 6 of the attachment arms 24, which means that the transverse support 6 can be rotated into the rear position when the traction needles are being positioned in the patient with a finder 13. Once the traction needle has been positioned, the transverse support 6 is rotated into the front position and locked into it with a knurled-head screw 18 to prevent the attachment arms 24 from swinging.

The guide carriage 8 (i.e. traction carriage) moves unobstructed on the lower supports 3 from the ankle end to the knee end. The guide carriage 8 comprises a bushing/sleeve (no reference numeral) for each of the lower supports 3, through which the lower supports 3 pass, and the sleeve has some kind of a locking screw (no reference numeral) with which the guide carriage 8 can be locked to the desired position on the lower support 3. On top of the lower sleeves, through which the lower support 3 passes, there is a separate attachment mechanism for the transverse supports of the attachment arms of the traction needles, which mechanism is attached to the lower sleeves. The attachment arms 24 of the traction needles of the ankle function in the same way as in attaching the knee, that is, the attachment arms 24 can be locked into the front position and the transverse support 6 has a groove 7 and the attachment arms 24 of the traction needle can thus be moved in the lateral direction and be locked into the desired position in the groove 7 with a knurled-head screw 32.

The upper supports 4 are usually at an approximately 5-7 cm higher level than the traction needles which are drilled through the tibia and attached to the attachment arms 22, 24 intended for the traction needles. The size of the leg is, therefore, irrelevant because the thickness of the human tibia is relatively constant in adult patients and the needle is usually drilled into the centre of the bone. The upper support 4 is, therefore, never in the way of imaging. The height of the ankle is on the same level as the attachment arms 22.

The transverse support 6' is made to move along the lower support 3 to allow the leg to be placed in traction and it is placed in position on the lower support 3 where the leg is in correct traction. For this purpose, the attachment arms 22 of the traction needle on the lower part of the tibia are on slide rails by means of the transverse support 6' and thus by pulling the attachment mechanism of the lower part, the ends of the tibia can be aligned.

The leg is placed in traction in the longitudinal direction and repositioned in the lateral direction by aligning the ends of the bone in the fracture site, for example, by using an X-ray dressing. An X-ray dressing is a lint-free cloth with a small piece of metal thread inside. The purpose of the metal thread in the cloth is (if these cloths are used in operations where a cloth is placed inside the body of a person), to enable finding the cloth by X-ray imaging thanks to the metal thread, because otherwise finding a cloth covered in blood is in practice impossible. The cloth is approximately 40 cm long and, when folded open, approximately 30 cm wide. The cloths can also be used to help in attaching the traction needles by placing the cloth transversely on the upper supports 4 so that the leg rests supported on the cloths. The leg will then not have to be supported when positioning the needles and the leg stays in place better.

There is a thread in the hole in the rings 27 of the transverse support 6' and the attachment arms 22, 24 can be held in place with a knurled-head screw 32 when the knurled-head screw 32 is tightened to the bottom of the groove, and when it is loosened, the attachment arms 22, 24 can again be moved simultaneously. It also prevents the attachment arms 22, 24 from turning downwards due to the weight of the leg because the screw is in the groove and not against a rounded surface. Similarly, the rings 27 in transverse support 6 comprise knurled-head screws not shown in FIG. 1, which are used for tightening in a corresponding manner.

Once the traction needles 20 are in place, the actual intramedullary nailing is carried out:

Next the surgeon makes an incision above the patella, through which the instruments used for the incision are inserted from under the patella inside the tibia.

A tissue protector is first placed under the patella, which tissue protector prevents the instruments from damaging the tissues and other important areas which are not relevant to the operation itself. All instruments required in the procedure, except the intramedullary nail, are inserted in the tibia through the tissue protector.

Next an entry opening is drilled in the bone with a slightly larger drill bit to a depth of approximately 4 cm in the longitudinal direction of the bone.

A guide wire which reaches all the way down to the ankle is then inserted in the bone. The guide wire has a thickness of approximately 2 mm-3 mm. It is used because the drill which is used to drill bone marrow away from obstructing the nail is hollow and the guide wire runs inside the drill bit to prevent the bit from penetrating the tissues at the fracture site and causing damage to the tissues.

After this, the bone marrow is gradually drilled, "reamed", away from inside the bone by changing the drill bit to a 1.5 mm larger one after each drilling until there is enough space for the intramedullary nail.

The intramedullary nail is then inserted in the bone with the help of the guide wire When the intramedullary nail is inside the bone, the guide wire is removed and the upper horizontal supports 4 are optionally removed from the sides of the device.

The intramedullary nail is now fixed inside the patient with screws. The upper supports 4 are then optionally removed, after which the leg can be detached from the attachment arms 22, 24 of the traction needles and the needle is cut from one side close to the skin and pulled out of the patient with flat nose pliers.

After these procedures, the incised wounds are closed and covered with wound dressings.

The invention claimed is:

1. A device for intramedullary nailing of a tibia, the device comprising:
a base;
a frame including vertical supports attached to the base, longitudinal horizontal supports attached to the vertical supports, and transverse horizontal supports attached to the vertical supports;
wherein the vertical supports include a first vertical support, a second vertical support, a third vertical support, and a fourth vertical support;
wherein the longitudinal horizontal supports include a first longitudinal horizontal support and a second longitudinal horizontal support, wherein the first longitudinal horizontal support is attached to the first vertical support and the second vertical support, and wherein the second longitudinal horizontal support is attached to the third vertical support and the fourth vertical support; and
wherein the transverse horizontal supports include a first transverse horizontal support and a second transverse horizontal support, wherein the first transverse horizontal support is attached to the first vertical support and the third vertical support, and wherein the second transverse horizontal support is attached to the second vertical support and the fourth vertical support;
a traction needle configured to be passed through the tibia;
a guide slidably coupled to one of the longitudinal horizontal supports, the guide including:
a first finder for adjusting a position of the traction needle in a lateral direction with respect to a joint surface of an upper part of the tibia; and
a second finder for adjusting the position of the traction needle in a vertical direction and for passing the traction needle through the tibia in a transverse direction of the tibia; and
attachment arms configured to be attached to the frame and to an end of the traction needle when the end is passed through the tibia in the transverse direction by using the guide.

2. The device according to claim 1, wherein the attachment arms include first attachment arms for attaching to the traction needle when inserted in a lower part of the tibia, wherein the first attachment arms are attached to a movable transverse horizontal support, the movable transverse horizontal support being slidably attached between the first longitudinal horizontal support and the second longitudinal horizontal support of the frame.

3. The device according to claim 2, wherein a guide carriage facilitates sliding movement of the movable transverse horizontal support along the first longitudinal horizontal support and the second longitudinal horizontal support.

4. The device according to claim 3, wherein the first longitudinal horizontal support and the second longitudinal horizontal support include upper longitudinal horizontal supports and lower longitudinal horizontal supports, wherein the lower longitudinal horizontal supports act as slide rails for the guide carriage.

5. The device according to claim 2, wherein the movable transverse horizontal support is configured to be turned forwards and backwards such that the first attachment arms are configured to be turned to forward and rearward positions.

6. The device according to claim 1, wherein the attachment arms include second attachment arms for attaching to the traction needle when inserted in an upper part of the tibia, wherein the second attachment arms are attached to the first transverse horizontal support of the transverse horizontal supports, the first transverse horizontal support being attached between two of the first vertical support and the third vertical support in a fixed manner.

7. The device according to claim 6, wherein the first transverse horizontal support is configured to be turned forwards and backwards such that the second attachment arms attached to the first transverse horizontal support is configured to be turned to forward and rearward positions.

8. The device according to claim 1, wherein the guide includes the first finder attached with a first sleeve and the second finder attached with a second sleeve for passing the traction needle through a lower part and an upper part of the tibia, respectively.

9. The device according to claim 7, wherein a vertical height adjustment part is connected to the guide, wherein the vertical height adjustment part is attached at its upper part to the first sleeve or to a separate attachment element in the guide, and at its lower part to the second sleeve, wherein the first finder and the second finder are in the guide at different adjustable heights.

10. The device according to claim 1, wherein the attachment arms are attached to the transverse horizontal supports by rings surrounding the transverse horizonal supports, the rings defining a threaded hole through which a screw can be tightened to the bottom of a groove to keep the attachment arms in place.

11. The device according to claim 1, wherein the first longitudinal horizontal support is spaced from the base at approximately the same distance as the second longitudinal horizontal support is spaced from the base.

* * * * *